United States Patent
Schmitt

(10) Patent No.: US 9,445,754 B2
(45) Date of Patent: Sep. 20, 2016

(54) METHOD AND SYSTEM FOR FITTING HEARING AIDS, FOR TRAINING INDIVIDUALS IN HEARING WITH HEARING AIDS AND/OR FOR DIAGNOSTIC HEARING TESTS OF INDIVIDUALS WEARING HEARING AIDS

(75) Inventor: Nicola Schmitt, Winterthur (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 14/412,313

(22) PCT Filed: Jul. 3, 2012

(86) PCT No.: PCT/EP2012/062908
§ 371 (c)(1),
(2), (4) Date: Dec. 31, 2014

(87) PCT Pub. No.: WO2014/005622
PCT Pub. Date: Jan. 9, 2014

(65) Prior Publication Data
US 2015/0208956 A1    Jul. 30, 2015

(51) Int. Cl.
*H04R 25/00* (2006.01)
*A61B 5/12* (2006.01)
*H04R 3/12* (2006.01)

(52) U.S. Cl.
CPC ............... *A61B 5/123* (2013.01); *H04R 25/30* (2013.01); *H04R 25/70* (2013.01); *A61B 5/121* (2013.01); *H04R 3/12* (2013.01); *H04R 25/554* (2013.01)

(58) Field of Classification Search
CPC ........................... H04R 25/70; H04R 2460/11
See application file for complete search history.

(56) References Cited

U.S. PATENT DOCUMENTS

| 5,197,332 A | 3/1993 | Shennib |
| 5,923,764 A * | 7/1999 | Shennib ................ A61B 5/121 381/23.1 |
| 6,118,877 A * | 9/2000 | Lindemann ............ H04R 25/70 381/23.1 |
| 6,671,643 B2 * | 12/2003 | Kachler ................ H04R 25/30 381/61 |
| 7,340,062 B2 | 3/2008 | Revit et al. |
| 7,372,970 B2 | 5/2008 | Ach-Kowalewski |
| 7,450,724 B1 * | 11/2008 | Greminger ............ H04R 25/70 381/312 |
| 8,433,087 B2 | 4/2013 | Nordahn et al. |
| 2005/0059904 A1 | 3/2005 | Chalupper et al. |

(Continued)

FOREIGN PATENT DOCUMENTS

| DE | 10 2009 048 071 A1 | 11/2010 |
| FR | 2 664 494 A1 | 1/1992 |
| WO | 2007/009287 A2 | 1/2007 |

*Primary Examiner* — Curtis Kuntz
*Assistant Examiner* — Ryan Robinson
(74) *Attorney, Agent, or Firm* — David S. Safran

(57) ABSTRACT

A hearing aid is fitted to an individual and/or the individual is trained in hearing with the hearing aid. In a first step a stimulus signal is provided. In a second step, the stimulus is presented to the individual. In a third step, a response of the individual in regard to the stimulus is obtained. In a fourth step a hearing aid parameter is adjusted based on the response. In an alternative or additional fourth step, a further stimulus signal is selected based on the response. The second step of presenting the stimulus signal comprises the sub-steps of obtaining a first and second signal based on the stimulus signal. In a further sub-step, the first signal is processed and presented by the hearing aid. Simultaneously, in a further sub-step, the second signal is presented by a supplementary loudspeaker for improving the stimulus presentation in regard to direct sound.

12 Claims, 2 Drawing Sheets

(56) References Cited

U.S. PATENT DOCUMENTS

| | | |
|---|---|---|
| 2007/0286403 A1 | 12/2007 | Gram et al. |
| 2008/0056518 A1* | 3/2008 | Burrows ................ H04R 25/70 381/314 |
| 2008/0124685 A1 | 5/2008 | Chalupper |
| 2008/0167575 A1* | 7/2008 | Cronin .................. A61B 5/121 600/559 |
| 2008/0187145 A1 | 8/2008 | Burrows et al. |
| 2009/0116657 A1 | 5/2009 | Edwards et al. |
| 2010/0111316 A1* | 5/2010 | Voix ....................... A61F 11/08 381/60 |

* cited by examiner

| | 1 | 2 | 3 | 4 | 5 | 6 | 7 | 8 | 9 | 10 | 11 | 12 | ... | N-1 | N |
|---|---|---|---|---|---|---|---|---|---|---|---|---|---|---|---|
| 0 | D | m | . | . | . | . | . | . | . | . | . | . | . | m | m |
| 10 | D | m | . | . | . | . | . | . | . | . | . | . | . | m | m |
| 20 | D | m | . | . | . | . | . | . | . | . | . | . | . | m | m |
| 30 | D | m | . | . | . | . | . | . | . | . | . | . | . | m | m |
| 40 | D | m | . | . | . | . | . | . | . | . | . | . | . | m | m |
| 50 | D | m | . | . | . | . | . | . | . | . | . | . | . | m | m |
| 60 | D | m | . | . | . | . | . | . | . | . | . | . | . | m | m |
| 70 | D | m | . | . | . | . | . | . | . | . | . | . | . | m | m |
| 80 | D | m | m | m | m | m | m | m | m | m | m | m | m | m | m |
| 90 | D | D | D | D | D | D | D | D | D | D | D | D | D | D | D |
| 100 | D | D | D | D | D | D | D | D | D | D | D | D | D | D | D |
| 110 | D | D | D | D | D | D | D | D | D | D | D | D | D | D | D |
| 120 | D | D | D | D | D | D | D | D | D | D | D | D | D | D | D |

METHOD AND SYSTEM FOR FITTING HEARING AIDS, FOR TRAINING INDIVIDUALS IN HEARING WITH HEARING AIDS AND/OR FOR DIAGNOSTIC HEARING TESTS OF INDIVIDUALS WEARING HEARING AIDS

BACKGROUND OF THE INVENTION

1. Field of the Invention

The invention relates to a method and a system which can be used for fitting hearing aids to individuals, for training individuals in hearing with hearing aids and/or for diagnostic hearing tests of individuals wearing hearing aids.

2. Description of Related Art

A hearing aid is a device for compensating a hearing loss of an individual using it. There are various tasks in regard to providing individuals with hearing aids. Two important ones are fitting and hearing training. During a fitting, a hearing aid is adapted to the hearing loss and preferences of the individual. During a hearing training, the individual learns to hear with the hearing aid. Typically, both tasks involve presenting calibrated acoustic stimuli to the individual and obtaining responses in regard to the stimuli to determine hearing performance, needs and preferences.

There are two distinct ways known for presenting stimuli to users of hearing aids: Firstly, stimuli may be presented by room loudspeakers, also referred to as free-field loudspeakers, thereby generating a sound field to which the hearing aid microphones are exposed. Such solutions are disclosed by Bismuth and Revit, as referenced below. Secondly, stimuli may be fed directly into the hearing aid circuit, such that there is no external sound field. Such solutions are commonly referred to as "in-situ" and are disclosed by Lindemann, Chalupper, Hempel and Heller, as referenced below.

French Patent FR 2664494 by Bismuth discloses a method for adjusting an auditory prostheses. Audiovisual scenes are presented to a patient in a soundproof audiometry booth.

U.S. Pat. No. 7,340,062 B2 by Revit et al. discloses assessing real-world performance of hearing aids. Sounds recorded in a real world acoustic environment are presented in a testing environment. A plurality of loudspeakers are located about a listening position or "sweetspot" where the test subject is placed.

U.S. Pat. No. 6,118,877 by Lindemann et al. discloses a hearing aid with in situ testing capability. The hearing aid has a tone generator for providing tones for diagnostic tests. A memory in the hearing aid may store real world sounds to simulate actual usage of the hearing aid. An external test tone generator may be coupled to the hearing aid by a wire.

European Patent Application EP 1 516 584 A1 and corresponding U.S. Patent Application Publication 2005/0059904 A1 by Chalupper et al. disclose a method to be used in the fitting of hearing aids. Chalupper avoids a soundproof booth by monitoring environment sounds and by determining if the noise level at the eardrum is sufficiently low for an in-situ audiometry, i.e., an audiometry in which the hearing aid presents the test tones.

European Patent Application EP 1 912 476 A2 corresponds and corresponding U.S. Patent Application Publication 2008/0124685a1 also by Chalupper disclose a method for training auditory skills, wherein the hearing aid presents sound examples to the user.

German Patent Application DE 10 2009 048 071 A1 by Hempel et al. discloses an improved in-situ fitting. Stimuli are filtered to simulate a predetermined room acoustics which is otherwise missing in in-situ stimuli.

International Patent Application Publication WO 2007/09287 A2 by Heller et al. discloses an in-situ audiometry. Sound samples are fed wirelessly into the hearing aid.

For the sake of completeness, it is mentioned here that feeding signals non-acoustically into hearing aids is not only known from the above in-situ testing, fitting and training methods, but also from real-life applications such as listening to a church service, communicating over a telephone or watching television. The latter is, for example, disclosed in European Patent Application EP 1 571 879 A2 and corresponding U.S. Pat. No. 7,372,970 B2. by Ach-Kowalewski.

An important topic for the present invention is the so called "direct sound". As used hereinafter, "direct sound" is to be understood as sound which passes directly, i.e., not through the hearing aid microphone, circuit and receiver, from the environment to the eardrum, for example, through a vent of the earpiece of the hearing aid and/or through a leakage path between the earpiece and the skin of the ear canal of the individual wearing the hearing aid. Accordingly, when the hearing aid is in-situ and switched off, there is only the direct sound in front of the eardrum. If it is switched on, there is a mixture of direct sound and receiver sound.

In particular, as used hereinafter, "direct sound" also includes reflected sound, i.e., sound which has be reflected prior to reaching the eardrum.

International Patent Application Publication WO 2007/099116 A2 and corresponding U.S. Pat. No. 8,433,087 B2 by Nordahn disclose a method of compensation for direct sound in hearing aids. A hearing aid gain is adjusted to a value that differs by a predetermined margin from a direct transmission gain calculated for the hearing aid.

SUMMARY OF THE INVENTION

It is an object of the invention to provide a method and a system for fitting at least one hearing aid and/or for training an individual in hearing with at least one hearing aid, which can be implemented in a relatively simple manner without the need for elaborated and/or costly equipment, such as a soundproof booth or very precisely calibrated devices, and which nevertheless allows to simulate real life acoustic situations relatively well.

These objects are achieved by a method and a system as described herein.

The invention is advantageous in that it can be carried out in relatively noisy environments, requires relatively little calibration and is precise in that it allows simulation of real life acoustic situations relatively well.

Stimulus presentation via the hearing aid blocks a significant part of the environment noise.

Hearing aids are generally at least partially pre-calibrated during their production, thereby reducing the amount of calibration needed at the site of carrying out the method according to the invention.

Supplementary loudspeakers open up the possibility to create direct sound, as it would be present in real life situations. Stimuli thereby can be presented at sound pressure levels above the output limitation of the hearing aid and at frequencies below and above the supported frequency range of the hearing aid. A realistic stimulus presentation is the basis for a precise adjustment of parameters during fitting and for a precise needs and progress assessment during adaptive training.

The hardware requires only standard components of which are practically all already present in a conventional fitting setup. The invention is therefore well suited for small offices, shops without separate fitting rooms, over the counter business cases and for use at home.

An aspect of the method of the invention is advantageous in that a fitting with a stimulus presentation as specified opens up the possibility to carry it out in a realistic, precise and efficient manner with reasonable requirements in regard to expertise, equipment and environment. The fitting can precisely account for effects of direct sound, acoustic coupling and vent loss which is often not the case in conventional audiogram formula based fittings.

Another aspect of the method of the invention is advantageous in that a hearing training with a stimulus presentation as specified opens up the possibility to carry it out in a realistic, precise and efficient manner with reasonable requirements in regard to expertise, equipment and environment. It can be well determined in regard to which hearing aspects performance is sufficient and which need to be trained more often.

Yet another aspect of the method of the invention is advantageous in that obtaining the stimulus by a device other than the hearing aid provides more flexibility and reduces the requirements in regard to the hearing aid. Transmitting a signal non-acoustically to the hearing aid provides a good resistance against environmental noise.

A further aspect of the method of the invention is advantageous in that such a positioning and configuration of the supplementary loudspeaker opens up the possibility to simulate accurately the effects of direct sound.

Another aspect of the method of the invention is advantageous in that the use of a headphone allows to avoid expensive, space consuming and difficult to calibrate room loudspeakers. It resolves the sweet spot issue, namely that a room loudspeaker calibration is only valid for a particular spot. The individual is not allowed to move. In the case of a headphone the position of the individual does not influence the measurement. Further, the headphone introduces as compared to room loudspeakers no significant acoustic delay.

Still another aspect of the method of the invention is advantageous in that a circumaural headphone is suited not only to be worn on top of in-the-ear hearing aids, but also on top of behind-the-ear hearing aids fully enclosing them. Further, the circumaural design opens up the possibility to significantly block ambient noise and to precisely calibrate the sound within the enclosed space. The method can be carried out in even more noisy environments.

A further aspect of the method of the invention is advantageous in that room loudspeakers prevent a headphone which is perceived by some individuals as being unnatural and/or discomforting.

Another aspect of the method of the invention is advantageous in that it providing a different signals opens up the possibility to provide dedicated signals for each, the at least one hearing aid and the at least one supplementary loudspeaker. The two devices can be separately calibrated. Further, their outputs can be coordinated. Unnecessary redundant presentation, artifacts, echoes, interferences and comb filter effects can be avoided. A redundant presentation means that portions of a stimulus are presented by both a hearing aid and a supplementary loudspeaker. This may have numerous disadvantages: The presentation level may not be well controllable due to superimposition and/or interferences. Interferences may also introduce artifacts. There may also be masking which makes the presentation by one of the devices useless. Avoiding useless presentations of stimulus portions by the hearing aid may save battery power in cases where the hearing aid is operated wirelessly, i.e., without a power supply cable.

An additional aspect of the method of the invention is advantageous in that complementary signals provide a good basis for obtaining a particular desired acoustic stimulus in front of the eardrum of the individual. The above mentioned redundant presentation is avoided.

Further features of the method of the invention are advantageous in that spectral filtering and loudness filtering are well suited to obtain both, a signal for presentation by a hearing aid as well as a complementary a signal for presentation by a supplementary loudspeaker. The capability of a hearing aid can usually be well described by a supported frequency range and a loudness limitation or a frequency dependent loudness limitation. Accordingly, such a filtering allows to assign stimulus portions well to the device best suited for presenting them.

Another aspect of the method of the invention is advantageous in that in opens up the possibility to reduce echo and interference artifacts which improves the naturalness of the presented stimuli. It also opens up the possibility to simulate intentionally artifacts which may occur in real life situations, for example, due to interferences between direct sound and receiver sound.

A further aspect of the method of the invention is advantageous in that a calibration of a supplementary loudspeaker opens up the possibility to improve the accuracy and enhance the range of the stimulus presentations. For example, it becomes possible to carry out tone audiogram measurements outside of the supported frequency and loudness range of the hearing aid. The spectrum of the stimuli can be better equalized. The naturalness of the presented stimuli and the acceptance by the individual is improved.

Additional embodiments and advantages of the invention are described in more detail with reference to the accompanying drawings which show exemplified embodiments.

DETAILED DESCRIPTION OF THE INVENTION

Figures 1, 3:
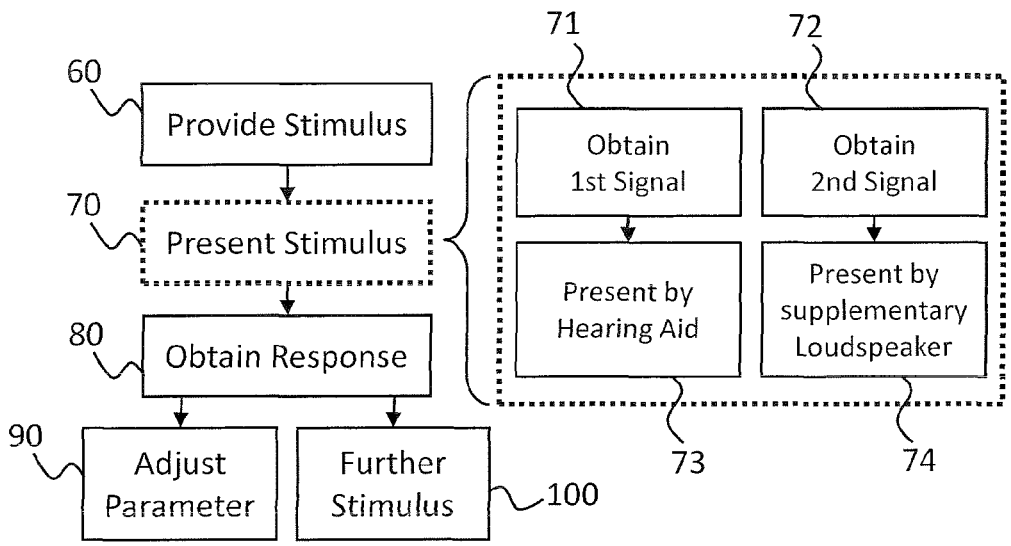
FIG. 1 is a flow diagram of an embodiment of a method for fitting and/or hearing training according to the invention.
FIG. 3 is a chart showing an example of which stimuli or which portions of a stimulus may be presented by the hearing aid and which which stimuli or which portions of a stimulus may be presented by the supplementary loudspeaker.

FIG. 1 is a flow diagram illustrating an example of a method for fitting a hearing aid to an individual and/or for training the individual in hearing with a hearing aid according to the invention. In a first step 60 a stimulus audio signal (also simply referred to as "stimulus signal" hereinafter) is provided by a stimulus signal provision means. In a second step 70 a stimulus presentation is carried out by presenting the stimulus signal and/or at least one signal obtained based on it to the individual. In a third step 80 a response of the individual is obtained in regard to the stimulus presentation. Steps 90 and 100 are alternatives, but can also be carried out both. In step 90 one or more signal processing parameters of the hearing aid are adjusted based on the response. A fitting may comprise multiple such adjustments. In step 100, the response is used in providing or identifying at least one further stimulus signal. An adaptive hearing training may comprise multiple such stimulus provisions.

The stimulus presentation of the second step 70 comprises several sub-steps. In sub-step 71, a first audio signal (also simply referred to as "first signal" hereinafter), which is based on the stimulus signal, is obtained. Optionally, a processed signal is obtained by processing the first signal by the at least one hearing aid. In sub-step 73, the first signal and/or, as the case may be, the processed signal is presented acoustically to the individual by the at least one hearing aid. In sub-step 72, a second audio signal (also simply referred to as "second signal" hereinafter), which is based on the stimulus signal, is obtained. Substantially simultaneously with sub-step 73 the second signal is presented by a supplementary loudspeaker for improving the stimulus presentation in regard to effects of direct sound. Since the stimulus signal is the basis for the first and second signal which are also in a way stimulus signals, it can also be referred to as primary stimulus signal.

It is noted that the sequences of steps described herein are exemplary and may be modified, i.e., the same steps may be carried out in other sequences, as far as it is feasible.

Figure 2:
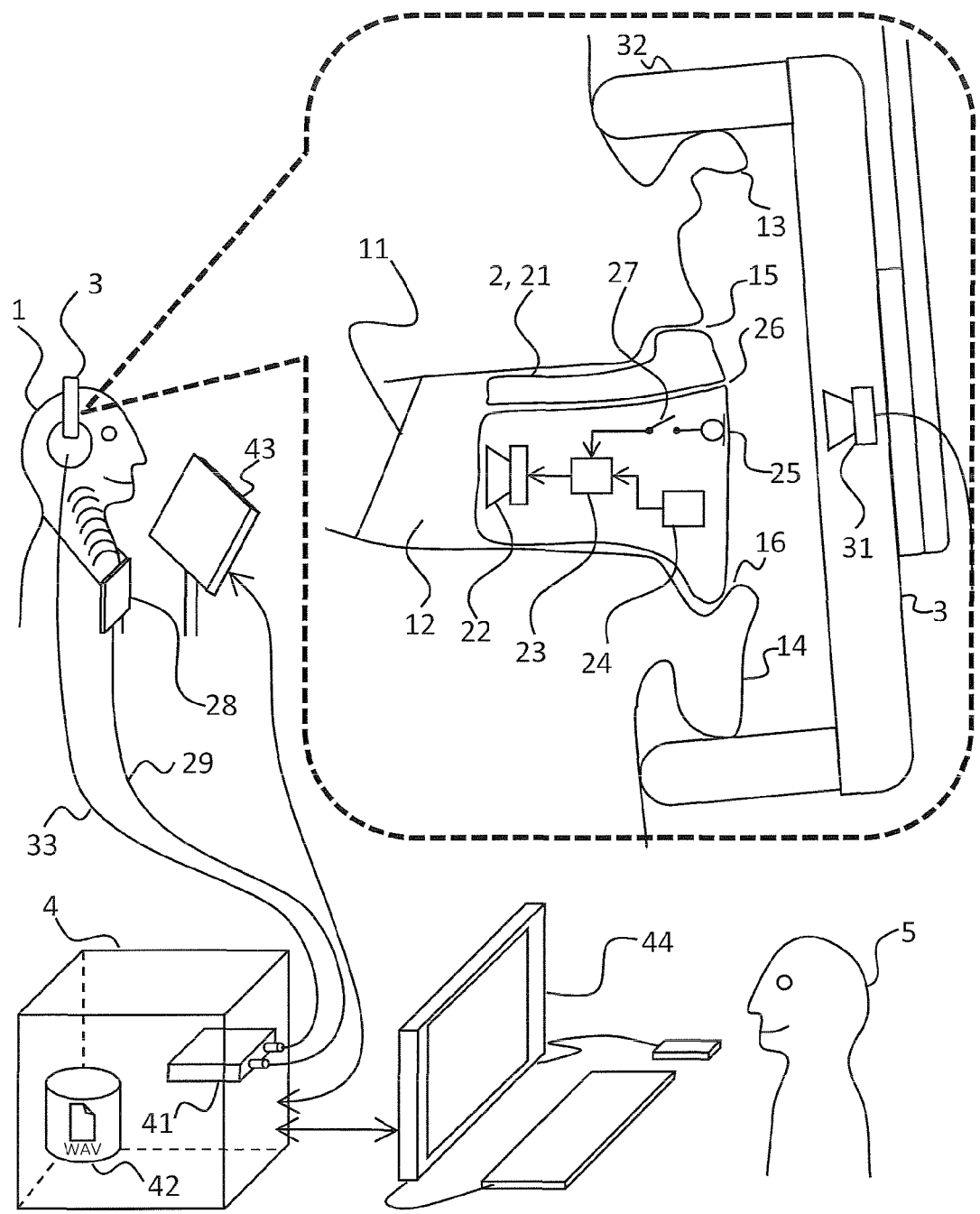
FIG. 2 is a schematic diagram of an embodiment of a system for fitting and/or hearing training according to the invention.

FIG. 2 is a diagram showing an example of a system for fitting a hearing aid and/or training an individual in hearing with the hearing aid according to the invention. The individual 1 wears a hearing aid 2 and a headphone 3. The individual 1 further wears a streaming device 28. An administrator 5 assists the individual 1. He or she operates a personal computer 4 by a user interface 44, namely a mouse, keyboard and screen. The individual 1 may communicate responses in regard to stimulus presentations verbally and/or by gestures to the administrator 5 who enters them by user interface 44. There is a further user interface 43, namely a touchscreen, which allows the individual 1 to enter responses directly.

The ear region of the individual 1 is shown in an enlarged sectional view. Hearing aid 2, pinna 12 and earlobe 14 are underneath an auricle encircling ear cup 32 of the headphone 3 which is of the circumaural type. The headphone 3 has preferably a closed back and blocks at least 10 dB, preferably at least 25 dB, of ambient noise.

The shown hearing aid 2 is of the in-the-ear type. It is fully integrated into an earpiece 21. The headphone 3 is worn and configured such that sound emitted by its loudspeaker 31 must pass through a vent 26 in the earpiece 21 and/or through a leakage path, such as path 15 or 16, between the earpiece 21 and a skin of the ear canal 12 before it reaches the eardrum 11 of the individual 1. The hearing aid 2 comprises a receiver 22 configured for emitting sounds into the ear canal 12, a signal processor 23, which may be configured for compensating a hearing loss of individual 1 and/or for performing sound cleaning, an antenna 24 for receiving a signal from the streaming device 28, as well as an environment microphone 25. The computer 4 comprises a sound card 41 as well as a sound storage 42, which may, for example, be a folder of a hard drive. The sound storage 42 can be regarded as a stimulus provision means. Hearing aid 2, headphone 3, computer 4 and streaming device 28 can be regarded together as a stimulus presentation means.

There is a first signal for presentation by the receiver 22 of the hearing aid 2 and a second signal for presentation by a supplementary loudspeaker, in the example, a loudspeaker 31 of headphone 3. The sound card 41 provides these two signals electrically. The first signal is fed by cable 29 to the streaming device 28 and from there wirelessly to hearing aid 2. The second signal is fed by cable 33 to the headphone 3. Cable 33 serve to feed a signal non-acoustically to the headphone 3. Cable 29 and streaming device 28 serve to feed a signal non-acoustically to the hearing aid 2. When feeding a signal non-acoustically to the hearing aid 2, the environment microphone 25 is preferably switched off or disconnected from the remaining hearing aid, physically or at least functionally by a disconnection means 27, which in practice may be a piece of software causing the signal processor 23 to ignore, mute or attenuate the corresponding sound data. Such a disconnection allows to prevent that the sound emitted by the supplementary loudspeaker 31 is sensed and amplified by the hearing aid 2. Preferably, the muting of the environment microphone 25 persists only as long as the stimulus presentation goes on, such that communication between the administrator 5 and the individual 1 is possible without hassle. The processor of the computer 4 together with a software executable by it serves to obtain the first and the second signal digitally, the sound card 42 in turn allows to obtain them in an analog manner.

Even though FIG. 2 shows only one environment microphone, there may be two or more such microphones, in particular a front and a back microphone in a directional microphone configuration.

Even though FIG. 2 shows only one hearing aid 2, it is noted that the invention can be applied to one or two hearing aids. If there is only one hearing aid, a headphone with a speaker only on one side may be sufficient. Otherwise a headphone having two speakers should be used, which is standard anyway. The term "headphone" herein is to be understood such that it covers both monaural and binaural implementations. The stimulus signal may be a mono, stereo, surround sound or sound field signal, comprising one, two or multiple channels. In the case of two hearing aids, the first signal may comprise a left and a right channel. In the case of one or two directional hearing aids, the first signal may comprise separate front and a back microphone signals. The second signal may also comprise one, two or multiple channels. The term "signal" herein is to be understood such that it covers all kinds of audio signals, such as mono signals comprising only one channel, stereo signals comprising two channels and surround sound, sound field or directional microphone signals having multiple channels, unless something else is indicated. Stimulus presentations can be carried out only on one side, on both sides subsequently and on both sides simultaneously.

Even though FIG. 2 shows a wired headphone 3 for the provision of the supplementary loudspeaker, the supplementary loudspeaker may also be a wireless headphone, headset or one or more room loudspeakers. Multiple room loudspeakers may be provided in a stereo or surround sound configuration, for example, a five point one ("5.1") configuration. In the case of a well-positioned individual and well calibrated room loudspeakers, it may be advantageous to carry out stimulus presentations fully with these. However, if the position of the individual is not well defined and calibration accuracy of the room loudspeaker is limited, feeding signals non-acoustically into the hearing aid is advantageous. Free-field loudspeakers may also be worn by the individual such that the positioning and "sweet spot" issue is less of a problem.

The supplementary loudspeaker may also be a receiver-style loudspeaker coupled directly or by a tube to a vent of the hearing aid. Vent-loss effects may be changed by such a setup. The change may have to be compensated by a special signal processing.

Generally, the "supplementary loudspeaker" is a loudspeaker which is added during the exceptional hearing aid used in fitting, hearing training or diagnostic hearing test, and which is not present during everyday use, for example, in a conversation at work or at home (for example, If a hearing aid has a permanent second receiver, such as to enhance low frequencies, this would not be a "supplementary loudspeaker" as understood herein).

Even though FIG. 2 shows an administrator 5, it is noted that the invention is also well suited for self-administered application at home or self-administered application in a self-service oriented shop.

Even though FIG. 2 shows a personal computer 4, other computing devices may be used. It may, for example, also be a tablet computer or an smart phone. Especially in the case of a self-administered home use, the computer 4 may be a multi-purpose device serving for further purposes, for example, telecommunication. The functionality of the computer may also be integrated in a hearing aid, hearing aid system or hearing aid remote control. Such a device or system would be provided with an output interface for the second signal, i.e., for connecting a supplementary loudspeaker. The interface may for example, be a Bluetooth interface or an electrical jack connector.

Even though FIG. 2 shows all components of the system close together, the system may be distributed geographically. For example, the hearing impaired individual 1, the administrator 5 and the sound storage 42 may all be at different locations. The individual 1 may be at work or at home, the sound storage 42 in a data center and the administrator 5 in a call center or acoustician shop.

Even though FIG. 2 shows an in-the-ear hearing aid, the invention can be carried out with other hearing aid types, in particular hearing aids for which one or more of the following applies: being completely-in-the canal; being deep-in-the-canal; having a behind-the-ear module; having a canal receiver, being suited for extended wear of more than one week; having a slim tube; having a custom ear-piece; having a one-size-fits-all or one-size-fits-many ear piece; having an open dome; having a vent; being unvented. While a "vent" typically is a bore in an ear piece, generally it may be any intentionally (i.e., by appropriate design) provided leakage path or paths in an ear piece, including for example, the openings of an open dome or trench like recesses in the shell of an ear piece.

Even though FIG. 2 shows a streaming device 28 connected with a wire 29 to the soundcard 41 and communicating wirelessly with the hearing aid 2, there are other ways for transmitting signals non-acoustically from a computer to a hearing aid. Streaming device and computer may communicate, for example, by Bluetooth.

There may be no streaming device, for example, if the hearing aid is Bluetooth compatible, if the electrical signal is fed directly from the computer to the hearing aid by an audio shoe, or if the signal is fed by an induction loop to a T-coil of the hearing aid.

Even though FIG. 2 shows a sound storage 42 for providing the stimulus signals, other ways of obtaining stimuli signals are possible. Stimulus signals may for example, also be generated in real-time by a synthesizer or by software executed by the computer. Further, the stimulus signal provision means may be integrated in the hearing aid. Stimuli signals may be recorded in real life situations, for example, by conventional recording equipment, but also by the hearing aid, in particular while the individual is wearing it in his or her personal environment. The sound storage may store only a primary stimulus signal, such that the first and second signal must be generated later or in real-time, e.g., by calculation and/or filtering. However, the first and second signal may be stored in the sound storage as well, or instead of the primary stimulus signal. It is also possible to not even record the primary stimulus signal, but instead to directly record the first and second signal. In such a case, the primary stimulus signal may only exist acoustically. The first signal may be based on a signal picked up with an environment microphone of a hearing aid, and the second signal may be based on a signal picked up with a canal or vent microphone of a hearing aid, preferably while the receiver of the hearing aid is switched off. In the case of synthesizing stimulus signals the first and second signal may be synthesized directly without synthesizing the primary stimulus signal.

Even though according to FIG. 2 the first signal is received by antenna 24 and fed into the signal processor 23, thereby obtaining a processed signal, it is also possible to feed the first signal into the signal path of the hearing aid after the signal processor 23. In this case loss compensation and sound cleaning may be done by the computer 4 by simulating the hearing aid processing. Such a solution has the advantage that the adjustment of signal processing parameters can be carried out within the computer thereby avoiding delays which may be encountered when sending adjustment instructions to the hearing aid. If the first signal comprises separate front and back signals, as required for a directional microphone based system, they should be fed into the signal path before the directional processing.

When using the system shown in FIG. 2 for fitting, there is preferably a means for adjusting one or more signal processing parameters of the hearing aid 2 based on the responses provided by the individual 1 in regard to the stimuli. For example, the stimulus may be a segment of speech, the response may be an instruction such as "louder", the signal processing parameter to be adjusted may be "volume", and the adjustment may be "+5 dB". The means for adjusting may comprise or consist of the computer 4 configured with a special fitting software, such as Phonak Target™, and a fitting interface device, such as NoahLink™. The fitting interface device and the streaming device 28 may be implemented together as one multifunctional device.

When using the system shown in FIG. 2 for an adaptive hearing training, there is preferably a means for providing or identifying one or more further stimulus signals based on responses of the individual in regard to past stimulus signals. The means for providing or identifying further stimulus signals may comprise or consist of the computer 4 configured with special hearing training software. A further stimulus signal may only be identified, while a first and second signal based on it are actually provided. The future training can be adapted in regard to the weaknesses identified in the past training. Further, it is possible to detect when the training has met its objective and can therefore be terminated.

FIG. 3 is a chart showing an example of which primary stimulus signals or which portions of a primary stimulus signal may advantageously be presented by the hearing aid receiver and which primary stimulus signals or which portions of a primary stimulus signal may advantageously be presented by the supplementary loudspeaker. Horizontally, there are frequency bands 1 to N, for example, according to the Bark scale. Vertically, there are loudness level ranges in which "0" stands for "0 to 10 dB HL" and "120" for "120 to 130 dB HL" while "D" is an abbreviation for "direct sound", i.e., sound presented by the supplementary loudspeaker, and "m" is an abbreviation for "mixed", i.e., sound that is presented by both the supplementary loudspeaker and the receiver of the hearing aid. A dot means that sound is only presented by the receiver of the hearing aid. The "portions of a primary stimulus signal" are the signal what remains when a primary sound (stimulus signal) is filtered or reduced to some extent.

The first and second signals are chosen regarding the different capabilities and/or calibration needs of hearing aid and supplementary loudspeaker which implies that they will be different from each other.

Preferably, the first and second signal are complementary, i.e., for example, if a sound of a particular loudness and frequency is presented fully by the hearing aid it will not be presented redundantly by the supplementary loudspeaker.

Generally, it is an objective to carry out fitting and/or hearing training in a way that resembles well real life situations. Accordingly, as in real life, typically the main part of the stimuli are presented by the hearing aid. The direct sound is only substantially relevant for loudness levels and frequencies which the hearing aid fails to present loud enough to compete with the direct sound. Accordingly in a special embodiment, the first signal and the second signal are obtained such that the first signal consists substantially of sounds which can be presented satisfactorily by the hearing aid and the second signal consists substantially of sounds which cannot be presented satisfactorily by the hearing aid. There may be small category of sounds for which it is best if they are included in both the first and second signal, namely sounds for which the above mentioned competition is without a clear winner. Typically, hearing aids perform well in the range from 1 to 8 kHz and up to 70 dB. However, these values may vary significantly depending on the hearing aid model, acoustic coupling and vent size.

As already indicated, what a hearing aid can present depends mostly on frequency and loudness. Accordingly, in a special embodiment, obtaining the first signal and/or the second signal comprises a spectral filtering. The spectral filtering is in particular carried out such that, at least in regard to sounds below a predefined loudness level, the first signal consists substantially of sounds within a predefined frequency range and/or the second signal consists substantially of sounds outside the predefined frequency range. Different predefined frequency ranges may be applied for the first and second signal, in particular to define two overlap frequency regions, the frequencies of which are contained in both signals. In the shown example band 2 is such a frequency region. The first and second signal may be attenuated in the overlap region to avoid an emphasis due to the superposition.

Alternatively or in addition, obtaining the first signal and/or the second signal may comprise a loudness filtering. The loudness filtering is in particular carried out such that, at least in regard to sounds within a predefined frequency range, the first signal consists substantially of sounds below a predefined loudness level and/or the second signal consists substantially of sounds above the predefined loudness level. Different predefined loudness levels may be applied for the first and second signal, for example, to define an overlap loudness region, the sounds of which are contained in both signals. In the illustrated example, 80 to 90 dB HL is such a region. The first and second signal may be attenuated in the overlap region to avoid an emphasis due to the superposition. Loudness filtering can be implemented in a full-spectrum manner, i.e., loud stimuli are fully presented by the supplementary loudspeaker, or in a band-wise manner, i.e., only frequency bands with a high sound pressure level are presented by the supplementary loudspeaker and others, for example, comprising only a background sound, are presented by the hearing aid.

It may be especially advantageous to obtain the first and second signal by a sharp separation, such that there are no overlap regions, neither in regard to frequency nor in regard to loudness in order to avoid interference and comb filter artifacts.

As already indicated, the environment microphone of the hearing aid is preferably switched off during stimulus presentations. However, if the sound presented by the supplementary loudspeaker comprises only sound the hearing aid is not capable of presenting, the switching off may be obsolete.

As already indicated, the first and second signal may be stereo, surround or multi-channel signals. For example, if the individual wears two different or differently fitted hearing aids it may be necessary to apply a different filtering for the right and left channels of the first signal. In a special case, the individual wears only one hearing aid, but in order to simulate a real life situation sound is presented on both sides. In this case, the channel of the first signal which is assigned to the side without a hearing aid is obsolete and may be mute or not existing, i.e., the first signal may comprise only one channel.

Presentation of stimuli by both, a hearing aid and a supplementary loudspeaker may result in echo effects due to different delays in the two transmission paths. Delays may for example, be introduced by converting digital representations of the first and/or second signal into analog representations as required for a standard headphone, room audio system or an analog streaming device input connector, by feeding the first signal non-acoustically to a hearing aid, by feeding the second signal non-acoustically to a supplementary loudspeaker, by processing the first signal by the hearing aid for loss compensation and/or sound cleaning, by propagation of sound waves from a receiver to an eardrum and by propagation of sound waves from a supplementary loudspeaker to a hearing aid or to an eardrum. Preferably, the first and second signal are synchronized such that they (and/or sounds resulting from first and second signal) are perceived as synchronous by the individual. However, it may also be an objective to simulate the real-world behavior of the hearing aid, which means that direct sound is earlier than the sound presented by the hearing aid. This is due to the processing delays in the hearing aid. The delay introduced by an analog hearing aid can be neglected. However, most hearing aids nowadays employ digital processing in the frequency domain, which introduces significant delays due to AD/DA and FFT/IFFT operations. Finally, in the case of audiovisual stimulus presentations it may be necessary to perform a further synchronization with the presented image. Such a synchronization is crucial in the case of lip-reading individuals.

It is to be understood that any such presentation of the first and second signal, which may involve some actual delay between the first and second signal due to signal processing requirements and/or differences in sound propagation paths, is to be considered as a "simultaneous" presentation of the first and second signal. Presentation of the first and second signal should be such that it enables the individual to perceive the first and second signal as synchronous.

In order to obtain precise results there is a need for calibration which may require additional method steps and/or system components. Both, presentation of the first signal by the hearing aid receiver and presentation of the second signal by the supplementary loudspeaker should be calibrated. The calibration is preferably a spectral calibration but may also be a simple overall loudness calibration.

The signal path of the first signal may comprise a sound card, a streaming device, a hearing aid processor and the hearing aid receiver. Preferably, a pre-calibrated sound card is used. Otherwise, it may be calibrated by playing calibration sounds and by measuring its electrical output. An on-site calibration of the hearing aid receiver is usually not necessary, because it is already calibrated in the factory. When sounds are fed non-acoustically to the hearing aid, for example, by a streaming device, it is important, that the automatic gain control is switched off. A sound card calibration in regard to the first signal can also be advantageously avoided if the signal is digitally fed into the hearing aid.

The signal path of the second signal may comprise a sound card, an amplifier and the supplementary loudspeaker. There are various ways to calibrate the presentation of the second signal.

In a first way, a microphone of the hearing aid is used to measure the sound emitted by the supplementary loudspeaker, in particular an environment, vent or canal microphone.

A second way is especially suited for a headphone as supplementary loudspeaker. A probe tube of a probe tube sound measurement device is inserted in the volume enclosed by the ear cups of the headphone, in particular such that the opening of the tube is in front of the vent opening of the hearing aid earpiece or in the ear canal.

A third way is especially suited for a room loudspeaker as supplementary loudspeaker. A conventional free field sound level meter is used to measure the sound level at the position of the individual while a calibration sound is played.

A fourth way is a subjective calibration. A first sound is presented in a calibrated manner by the hearing aid. A second sound is presented by the supplementary loudspeaker. The sounds are adjusted to equal loudness by, or based on responses of, the individual wearing the hearing aid.

The sound used for calibrations may be a special calibration sound as for example, a broadband noise or a sine sweep. However, the calibration may also be carried out during stimulus presentations of fitting or hearing training. Accordingly, stimuli may be used as calibration sounds.

The system or components of it may be calibrated in the factory and/or on-site. If multiple users are provided with an identical equipment it may be sufficient to carry out the calibration only once with a master equipment and use the data obtained thereby for calibrating the equipment provided to the individual users. An on-site calibration has the advantage that the system may comprise arbitrary components, as for example, a non-standard sound card.

Besides of the calibration issue, it may also be advantageous to monitor if the environment is sufficiently quiet for carrying out the method. Such a monitoring can be done by a microphone connected to the soundcard of the computer, by a microphone of a streaming device or a microphone of the hearing aid, in particular an environment, vent or canal microphone.

The invention is especially advantageous in regard to individuals with a severe or profound hearing loss (typically, hearing losses above 70 dB HL are considered as severe or profound). The supplementary loudspeaker allows to present stimuli which are too loud to be presented by the hearing aid. This allows to simulate additional hearing situations which may occur in real life. Fitting and training can therefore be improved.

Stimuli suitable for the present invention are, for example, pure tones as used in conventional audiogram measurements, noises, wobble tones, narrow band tones, logatomes, phonemes, words, nonsense syllables, sentences, standard recordings of typical real life situations and recordings of real life situations done by the individual her- or himself, or her or his hearing system respectively. The stimulus may also be audiovisual such that the stimulus provision means provides in addition to the first and second signal, which are audio signals, a visual signal and presents according images or moving images to the individual.

An advantageous embodiment of method and system according to the invention is fitting hearing aids, i.e., in adjusting signal processing parameters of the hearing aid, as for example, volume or tonal balance. In this case, the stimulus may be a sound sample of a so called sound parcours. A sound parcours may comprise different simulated real-live scenes, in particular at least one for each hearing program, for example, one for speech in quiet, one for noise, one for speech in noise and one for music. However, there may be more sophisticated scenes such as music in a concert hall and pop music from a radio, a female speaking in the back seat of a car or a male speaking in a television newscast. The response obtained from the individual may be a rating such as "poor", "good" and "very good" or a preference such as "just right", "softer", "louder", "brighter", "duller" or the like.

Accordingly, a user interface for obtaining such a response may for example, be a conventional volume and/or tone control, which may be implemented as one or more virtual or physical slider, up-down rocker switch or the like on a remote control, smartphone, touchscreen or similar devices. As known from a volume control, stimulus presentation and response are in this case not two distinct steps, but rather ongoing simultaneous processes. The response may also refer to two subsequent stimulus presentation and indicate a relative preference such as "A is equal to B", "A is better than B" or vice versa. Typically, the same stimulus is presented more than once with different hearing aid parameter settings, such that the user can compare which setting is best. The stimulus may also be stationary and enduring, for example, as provided by a speaker continuously reading a text, such that the user can try out different parameter settings while the stimulus is being presented. Instead of directly manipulating hearing aid parameter settings, the change to be evaluated can be integrated in the stimuli. For example, a second stimulus may be 10 dB louder than a first stimulus. If the user prefers the second stimulus the hearing aid is adjusted by increasing the volume by 10 dB.

A further advantageous embodiment of the method and system according to the invention is an adaptive hearing training. Such a training may be employed to teach an individual how to hear with a new hearing aid. A training may be adaptive simply in that identifies based on responses when the training objective has been achieved and the training can be terminated. However, the training may also be adaptive in that weaknesses of the aided individual are identified. Special training lessons may then focus on eliminating these weaknesses. For example, the training may comprise a logatome test, in which the individual must identify logatomes such as ASA, ASHA, AFA, ADA, AGA, etc. A result of this test may be a weakness in distinguishing ASA and ASCHA. The training may then provide a special lesson for training the distinction of ASA and ASCHA.

The response obtained from the individual may for example, be a simple reaction, such as pushing a button, whenever something has been heard, a selection what has be heard from a multitude of choices, entering what has been heard without having predefined choices, identifying same or different sounds, subjective and perceptive ratings such as "easy-" and "difficult to understand" or "perceived as soft", "-medium" and "-loud" or adjustment instructions such as "the sound must be a bit louder in order to be perceived as medium loud", or "-to be perceived as easy to understand".

In a further advantageous embodiment, the above described fitting and training are combined. In a first step, a hearing issue may be identified by stimulus presentations and obtaining responses. In a second step, an algorithm may assess if the issue can be better resolved by fitting or training, which is then carried out in a third step. Alternatively, the primary task is a fitting or training. If an issue cannot be sufficiently resolved by the primary task the complementary task is carried out, namely in the case of fitting a training and vice versa.

In addition to obtaining subjective responses from the individual, it is also possible to measure the sound resulting from a stimulus presentation in the ear canal objectively, for example, with a canal microphone or a probe tube microphone device. Even though the method claims of the present document cover only embodiments comprising the step of obtaining a response of the individual, it is herewith disclosed that it is also possible to apply the principle of enhancing hearing aid sound presentations by supplementary loudspeaker based direct sound provision in purely objective measurements.

Even though only fitting and training applications have been mentioned so far, the principle of enhancing hearing aid sound presentations by supplementary loudspeaker based direct sound provision can also be applied in the presentation of stimuli for diagnostic hearing tests without subsequent fitting or training.

The diagnostic hearing test may in particular be "aided diagnostics" in which the hearing performance of an individual using a hearing aid is determined. Such a test can be used for comparing hearing aids, for example, of different manufacturers. For this, the test is carried out twice with the same individual, but with different devices. The test may be a speech audiometry, such as the "Oldenburger Satztest". The test may be of a kind, which is normally carried out as free field audiometry, but is according to the above described principles carried out partially in-situ.

The described embodiments are meant as examples and not intended to limit the invention.

What is claimed is:

1. A method comprising the steps of:
   providing a stimulus audio signal by a stimulus signal provision means (42);
   obtaining a first audio signal and a second audio signal different from the first audio signal, which both are based on said stimulus audio signal;
   presenting said first audio signal, acoustically to an individual (1) by a receiver (22) of at least one hearing aid (2) worn by said individual and simultaneously presenting said second audio signal as direct sound acoustically to said individual (1) by at least one supplementary loudspeaker (31);
   receiving a response of said individual (1) in regard to said acoustic presentation of said first and second audio signal; and
   using said response in at least one of a process of fitting said at least one hearing aid to said individual; a process of training said individual in hearing with said at least one hearing aid, and a diagnostic hearing test of said individual wearing said at least one hearing aid;
   wherein said first audio signal and said second audio signal are different and wherein said first and/or said second audio signal is obtainable by filtering said stimulus signal, and wherein said first audio signal and said second audio signal are substantially complementary such that adding said first and second audio signal results substantially in said stimulus signal.

2. The method of claim 1, wherein said response is used in adjusting one or more signal processing parameters of said at least one hearing aid (2).

3. The method of claim 1, wherein said response is used in providing or identifying at least one further stimulus signal (1).

4. The method of claim 1, wherein said first audio signal is primarily obtained in a device (4) other than said at least one hearing aid (2) and is feed by a feeding means (28, 29) non-acoustically to said at least one hearing aid (2).

5. The method of claim 1, wherein said at least one supplementary loudspeaker (31) is positioned and configured such that sound emitted by it must pass through a vent (26) of an earpiece (21) of said at least one hearing aid (2) and/or through a leakage path (15) between said earpiece (21) and a skin of an ear canal (12) of said individual (1) before reaching an eardrum (11) of said individual (1).

6. The method of claim 1, wherein said at least one supplementary loudspeaker (31) is comprised in a headphone (3) worn by said individual (1).

7. The method of claim 6, wherein said headphone (3) is a circumaural headphone, and is designed to block at least 10 dB, preferably at least 25 dB, of ambient noise to have a closed back and/or to have one or two auricle encircling ear cups (32).

8. The method of claim 1, wherein said at least one supplementary loudspeaker (31) is at least one room loudspeaker, such as in a stereo or a surround sound configuration.

9. A method comprising the steps of:
   providing a stimulus audio signal by a stimulus signal provision means (42);
   obtaining a first audio signal and a second audio signal different from the first audio signal, which both are based on said stimulus audio signal;
   presenting said first audio signal, acoustically to an individual (1) by a receiver (22) of at least one hearing aid (2) worn by said individual and simultaneously presenting said second audio signal as direct sound acoustically to said individual (1) by at least one supplementary loudspeaker (31);
   receiving a response of said individual (1) in regard to said acoustic presentation of said first and second audio signal; and
   using said response in at least one of a process of fitting said at least one hearing aid to said individual; a process of training said individual in hearing with said at least one hearing aid, and a diagnostic hearing test of said individual wearing said at least one hearing aid;
   wherein said first audio signal and said second audio signal are different, wherein said first and/or said second audio signal is obtainable by filtering said stimulus signal, and wherein obtaining said first audio signal and/or said second audio signal comprises a spectral filtering such that at least for sounds below a predefined loudness level said first audio signal consists substantially of sounds within a predefined frequency range and/or said second audio signal consists substantially of sounds outside said predefined frequency range.

10. A method comprising the steps of:
providing a stimulus audio signal by a stimulus signal provision means (42);
obtaining a first audio signal and a second audio signal different from the first audio signal, which both are based on said stimulus audio signal;
presenting said first audio signal, acoustically to an individual (1) by a receiver (22) of at least one hearing aid (2) worn by said individual and simultaneously presenting said second audio signal as direct sound acoustically to said individual (1) by at least one supplementary loudspeaker (31);
receiving a response of said individual (1) in regard to said acoustic presentation of said first and second audio signal; and
using said response in at least one of a process of fitting said at least one hearing aid to said individual; a process of training said individual in hearing with said at least one hearing aid, and a diagnostic hearing test of said individual wearing said at least one hearing aid;
wherein said first audio signal and said second audio signal are different, wherein said first and/or said second audio signal is obtainable by filtering said stimulus signal, and wherein obtaining said first audio signal and/or said second audio signal comprises a loudness filtering such that at least for a predefined frequency range said first audio signal consists substantially of sounds below a predefined loudness level and/or said second audio signal consists substantially of sounds above said predefined loudness level.

11. A method comprising the steps of:
providing a stimulus audio signal by a stimulus signal provision means (42);
obtaining a first audio signal and a second audio signal different from the first audio signal, which both are based on said stimulus audio signal;
presenting said first audio signal, acoustically to an individual (1) by a receiver (22) of at least one hearing aid (2) worn by said individual and simultaneously presenting said second audio signal as direct sound acoustically to said individual (1) by at least one supplementary loudspeaker (31);
receiving a response of said individual (1) in regard to said acoustic presentation of said first and second audio signal; and
using said response in at least one of a process of fitting said at least one hearing aid to said individual; a process of training said individual in hearing with said at least one hearing aid, and a diagnostic hearing test of said individual wearing said at least one hearing aid;
wherein said first audio signal and said second audio signal are different, wherein said first and/or said second audio signal is obtainable by filtering said stimulus signal, and
comprising the step of at least partially synchronizing said first and said second audio signal in regard to an acoustic perception of resulting sounds by said individual (1), compensating one or more of the following:
a delay introduced by converting a digital representation of said first audio signal and/or said second audio signal into an analog representation;
a delay introduced by feeding said first audio signal non-acoustically into said at least one hearing aid (2);
a delay introduced by feeding said second audio signal non-acoustically to said at least one supplementary loudspeaker (31);
a delay introduced by a processing of said first signal by said at least one hearing aid (2), said processing in particular comprising a hearing loss compensation and/or a sound cleaning;
a delay introduced by a propagation of sound waves from said receiver (22) of said at least one hearing aid (2) to an eardrum (11) of said individual (1);
a delay introduced by a propagation of sound waves from said at least one supplementary loudspeaker (31) to said at least one hearing aid (2) or an eardrum (11) of said individual (1).

12. The method of claim 1, further comprising the step of calibrating a sound output of said at least one supplementary loudspeaker (31), such as by at least one of probe tube measurements, in particular in front of a vent (26) of said earpiece (21) and/or in an ear canal (12) of said individual (1);and evaluating a signal provided by at least one microphone (25) of said at least one hearing aid (2), in particular an environment microphone (25), a vent microphone and/or a canal microphone; carrying out measurements with an identical equipment.

* * * * *